(12) United States Patent
Woodward (10) Patent No.: US 11,140,302 B2
(45) Date of Patent: Oct. 5, 2021

(54) COMBINED CAMERA AND WEARABLE RING FOR HOLDING A CAMERA

(71) Applicant: Charles Hudson, St Saviour (JE)

(72) Inventor: Harley Woodward, Trinity (JE)

(73) Assignee: Charles Hudson, St Saviour (JE)

( * ) Notice: Subject to any disclaimer, the term of this patent is extended or adjusted under 35 U.S.C. 154(b) by 0 days.

(21) Appl. No.: 17/105,593

(22) Filed: Nov. 26, 2020

(65) Prior Publication Data

US 2021/0136262 A1 May 6, 2021

Related U.S. Application Data

(63) Continuation-in-part of application No. 16/379,035, filed on Apr. 9, 2019, now Pat. No. 10,972,644.

(51) Int. Cl.

| | |
|---|---|
| *H04N 5/225* | (2006.01) |
| *H04N 7/18* | (2006.01) |
| *H04N 5/232* | (2006.01) |
| *A61B 5/00* | (2006.01) |
| *A61F 5/41* | (2006.01) |

(52) U.S. Cl.
CPC ......... *H04N 5/2253* (2013.01); *A61B 5/0077* (2013.01); *H04N 5/232* (2013.01); *H04N 7/181* (2013.01); *A61B 5/6813* (2013.01); *A61F 5/41* (2013.01); *A61F 2005/414* (2013.01)

(58) Field of Classification Search
CPC ...... H04N 5/2253; H04N 7/181; H04N 5/232; H04N 7/185; H04N 5/2257; H04N 5/2252; A61B 5/0077; A61B 5/6813; A61F 5/41; A61F 2005/414; G03B 17/561; G03B 17/02
See application file for complete search history.

(56) References Cited

U.S. PATENT DOCUMENTS

| | | | |
|---|---|---|---|
| 2003/0045799 A1* | 3/2003 | Bazin ..................... | G01N 21/84 600/476 |
| 2015/0036311 A1* | 2/2015 | Mullani ................. | A61B 5/441 362/19 |

* cited by examiner

*Primary Examiner* — Yogesh K Aggarwal
(74) *Attorney, Agent, or Firm* — Inventa Capital PLC (57) ABSTRACT

A wearable device, such as a ring, is used to be worn on at least one part of a human body. A wearable device includes a body having a bottom surface and a top surface, an opening defined between the top surface and the bottom surface. The opening is used to receive therethrough and hold the at least one part of the human body. A pocket is defined in the body between the opening and the top surface for holding the camera presenting an activation button to turn on and turn off the camera. The body includes a membrane defined in the top surface of the body.

12 Claims, 13 Drawing Sheets

COMBINED CAMERA AND WEARABLE RING FOR HOLDING A CAMERA

FIELD OF THE INVENTION

The present invention relates to the field of sex toys, in particular to a penis erection support ring that assists a penile function when mounted on a penis of a male during sexual intercourse.

BRIEF DESCRIPTION OF THE INVENTION

Various sex toys have been around since the beginning of recorded history. Common older types of penetrative sex toys include: dildos, Ben Wa balls, horseshoes, double penetration dildos, strap-on dildos, kegel exercisers, motorized sex machines, butt-plugs, anal beads, and prostate massagers; any of which can be fitted with vibrators. These sex toys are traditionally made of silicon, rubber, hard plastic, metal, glass, or cyber skin; although stranger materials can and are used.

One of the most popular sex toys is a cock ring. The cock ring is a ring worn around the penis, usually at the base. The primary purpose of wearing the cock ring is to restrict the flow of blood from the erect penis in order to produce a stronger erection or to maintain an erection for a longer period of time. When used in cases of erectile dysfunction (ED), they are known by various other names, such as erection rings and tension rings. The cock ring may be used for medical purposes. A man may wear an erection ring because he has erectile dysfunction (ED). When used for ED, a purpose-designed vacuum pump is used to produce an erection by simple mechanical and hydrodynamical action in spite of vascular or nerve damage, and the ring is slid off the pump's cylinder onto the base of the penis to maintain the erection before it is lost. The cock ring is also used for recreational purposes. The cock ring may be used during sex or masturbation to prolong or enhance erections, delay orgasm, or for the sensation of tightness and engorgement that wearing one produces; vibrating models apply vibration to the base of the user's penis and to their partner.

To the extent as being effective, there is always a need for new and improved systems, devices, and methods that can improve and prolong sexual pleasure and add new excitement to sexual live of partners. The present invention aims to solve this problem by simple and convenient means.

SUMMARY OF THE INVENTION

A wearable device, such as a ring, includes a body used to be worn on at least one part of a human body. A wearable device includes a body having a bottom surface and a top surface, an opening defined between the top surface and the bottom surface. The opening is used to receive therethrough and hold the at least one part of the human body, such as a finger or a penis. A pair of pockets are defined in the body between the opening and the top surface for holding two cameras each presenting an activation button to turn on and turn off the cameras. These two cameras will be used in order to capture action facing opposite sides of the wearable device. In alternative embodiment of the present invention, the pocket is replaced with an upper opening to receive a 360-degree camera in order to capture all action around the wearable device.

The body includes a membrane defined in the top surface of the body wherein the activation button does not extend through the membrane as the camera is disposed in the pocket to turn off or turn on the camera as the body is worn on the penis or the finger. The top surface has a first section presenting a first thickness and a second section presenting a second thickness, being thinner that the first thickness. The membrane is located around the second thickness. When the activation button is activated, the membrane extends from an idle position as the first section and the section are located along and coplanar with one another to an activating position as the membrane extends to and frictionally engages the activation button to turn on the camera and returning back to the idle position.

An advantage of the present invention is to provide an innovative cock ring designed as a silicone ring housing that is wearable on a penis or dildo.

Another advantage of the present invention is to provide the innovative cock ring, which is made in a way that it houses a WiFi compatible camera which is controlled, viewed via a mobile application.

Still another advantage of the present invention is to provide the innovative cock ring used for sexual stimulation as well as recording intimate moments at a completely new angle/POV.

Yet another advantage of the present invention is to provide the innovative cock ring used for sexual stimulation as well as recording intimate moments wherein the camera will allow to capture environment around the camera.

The objects and advantages of the present invention will be more readily apparent from inspection of the following specification, taken in connection with the accompanying drawing, wherein like numerals refer to like parts throughout and in which an embodiment of the present invention is described and illustrated.

The exact manner in which the foregoing and other objects and advantages of the invention are achieved in practice will become more clearly apparent when reference is made to the following detailed description of the preferred embodiments of the invention described in detail in the following specification and shown in the accompanying drawings, where in like reference numbers indicate corresponding parts throughout.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

FIGS. 1 through 13, illustrate a wearable device, such as a ring, generally shown at 10. The device 10 is designed as a silicone ring housing or a body, generally indicated at 12, which is wearable on a penis or dildo P, it is made in a way that it houses a WiFi compatible camera 14, which is controlled, viewed via a mobile application. The device 10 is used for sexual stimulation as well as recording intimate moments at a completely new angle and point of view.

As used herein, the singular forms "a," "an," and "the" include plural referents unless the context clearly dictates otherwise. Furthermore, as used herein, the term "based on" includes based at least in part on. Thus, a feature that is described as based on some cause, can be based only on that cause, or based on that cause and on one or more other causes.

It will be apparent that multiple embodiments of this disclosure may be practiced without some or all of these specific details. In other instances, well-known process operations have not been described in detail in order not to unnecessarily obscure the present embodiments. The following description of embodiments includes references to the accompanying drawing. The drawing shows illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

Alluding to the above, for purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

Referring back to FIGS. 1 through 13, the wearable device 10 includes the body 12 used to be worn on at least one part of a human body, such as the penis P. The body 12 includes a bottom surface 16 and a top surface 18. An opening 20 is defined between the top surface 18 and the bottom surface 16. The opening 20 is used to receive therethrough and hold the at least one part of the human body, such as a finger or the penis P.

The body 12 includes a pocket, generally indicated at 22, is defined in the body 12 between the opening 20 and the top surface 18 for holding the camera 14 presenting an activation button 24 to turn on and turn off the camera 14. The body 12 includes a slot 28 defined in the top surface 18 of the body 12 and extending to the pocket 22 to receive the activation button 24 extending through the slot 28 as the camera 14 is disposed in the pocket 22 to turn off or turn on the camera 14 as the body 12 is worn on the penis P or the finger.

Figure 9:
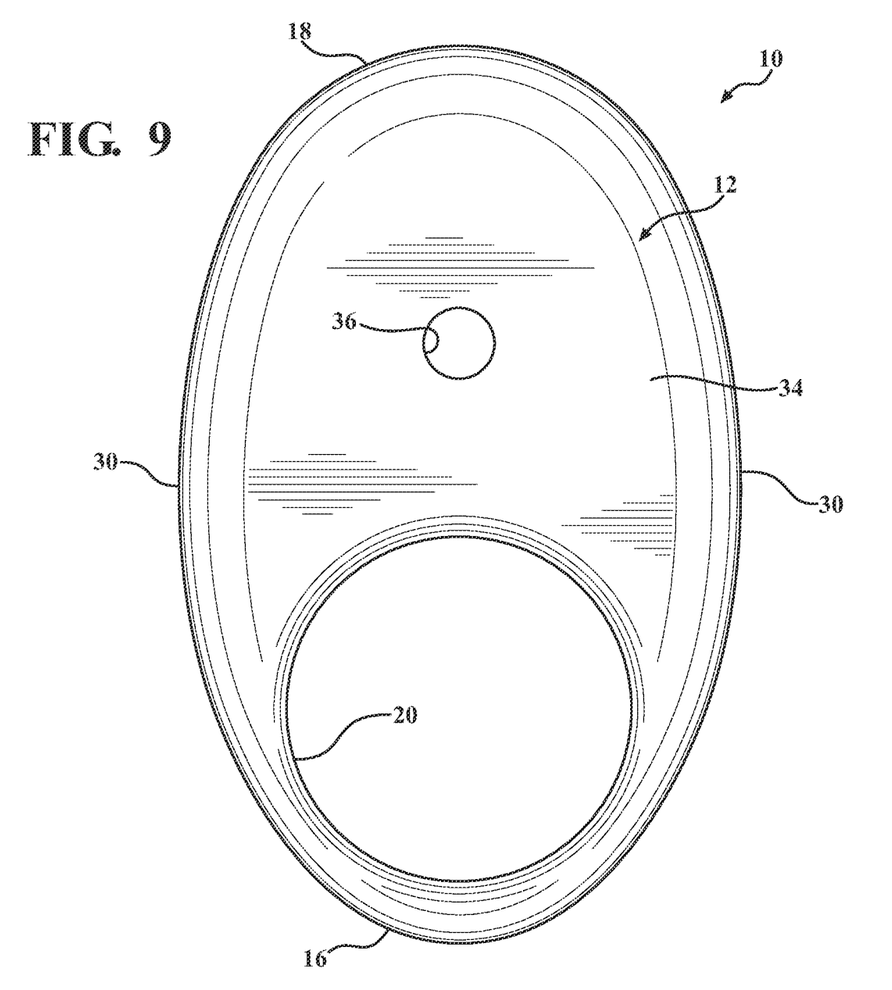
FIG. 9 is a rear side view of the wearable ring for holding the camera.
Figure 10:
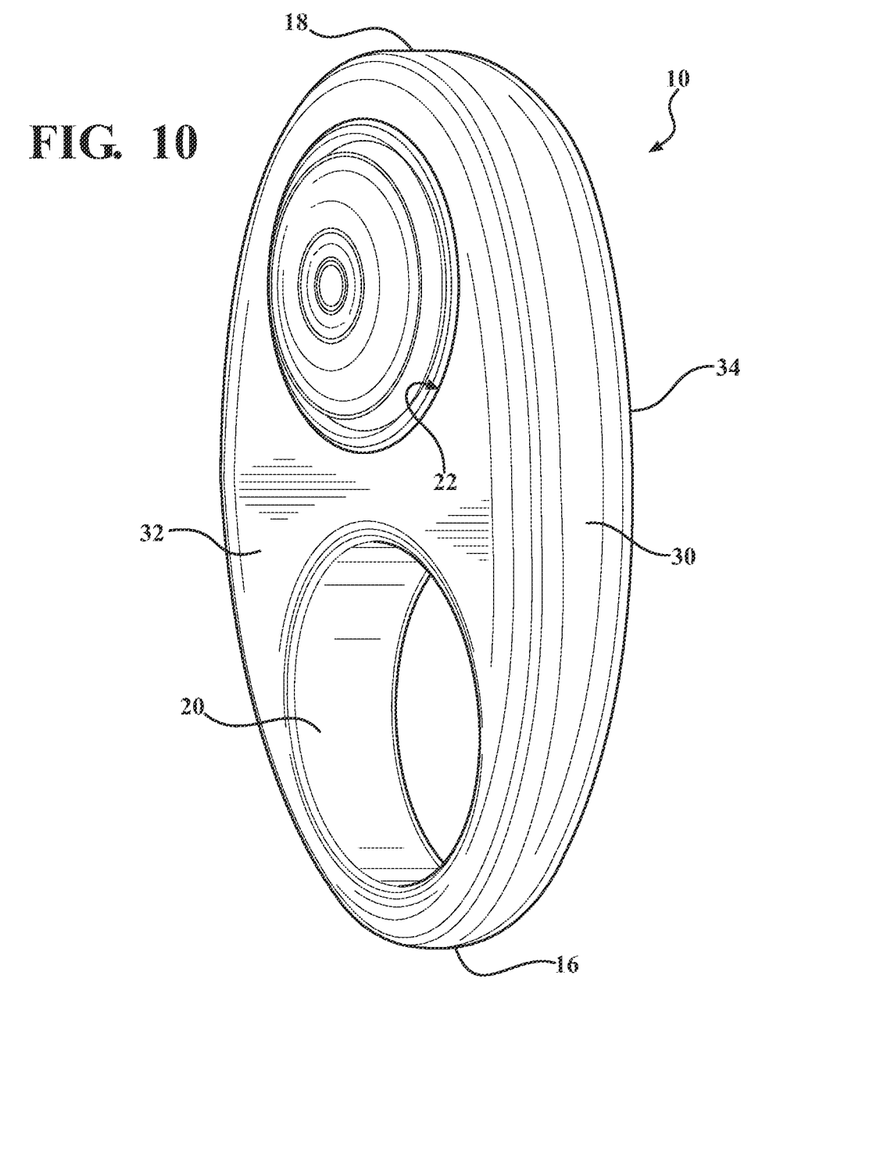
FIG. 10 is a perspective view of the wearable ring for holding the camera.
Figure 11:
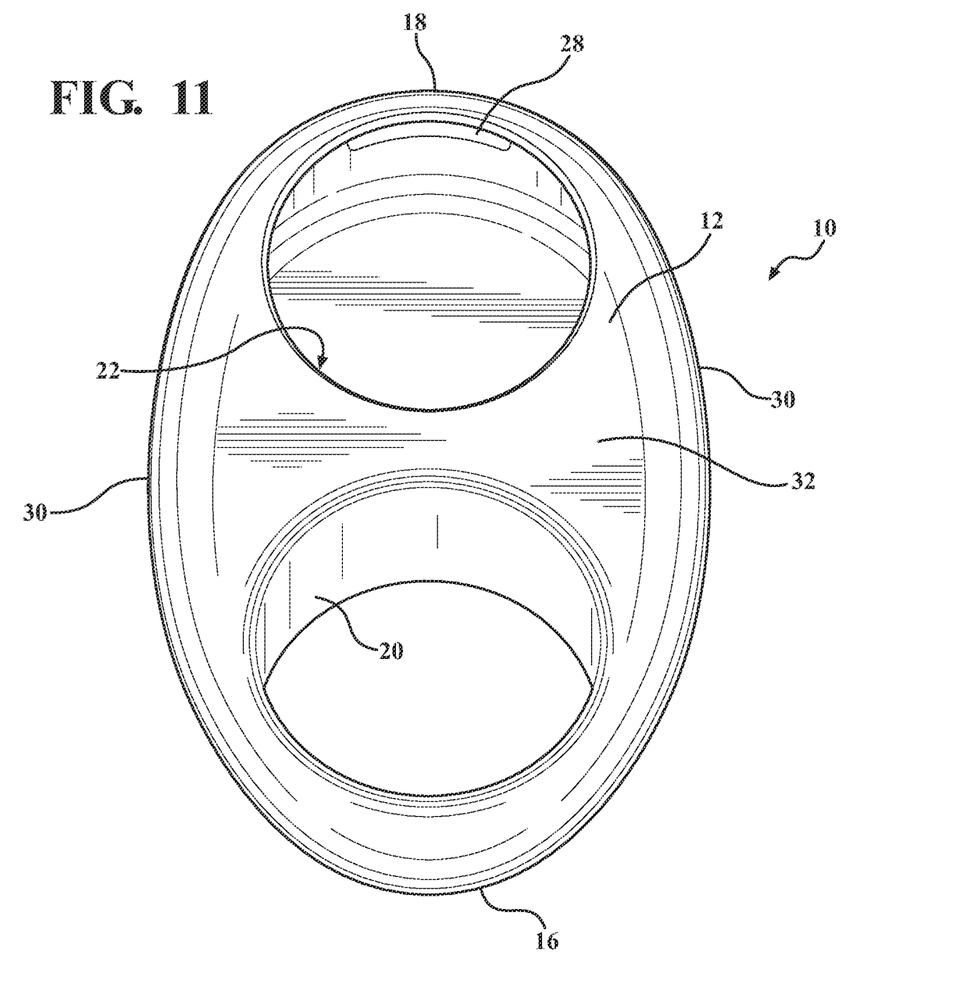
FIG. 11 is a perspective view of the wearable ring for holding the camera taken from the bottom.
Figure 12:
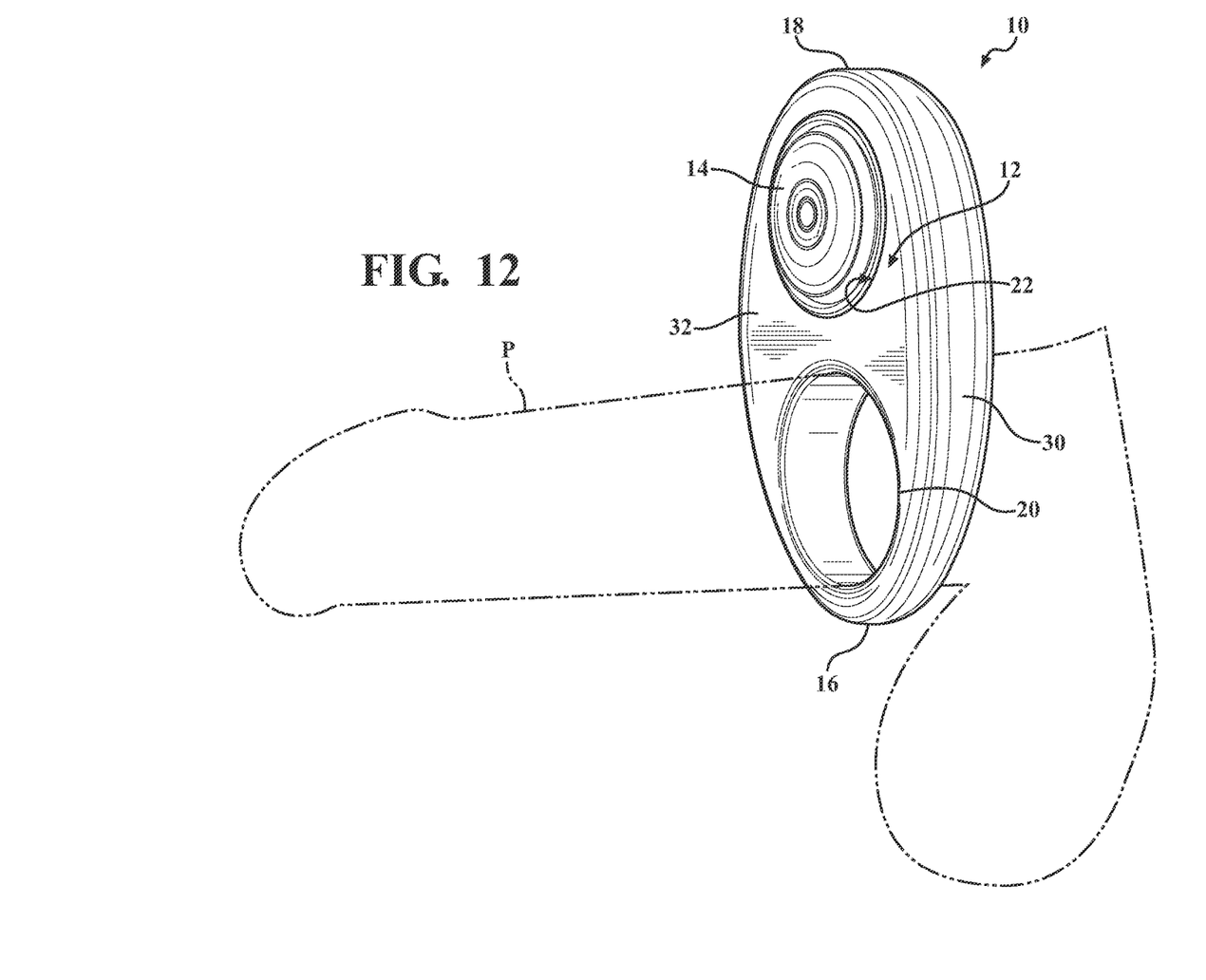
FIG. 12 is a perspective side view of the wearable ring for holding the camera positioned on a part of a human body.
Figure 14:
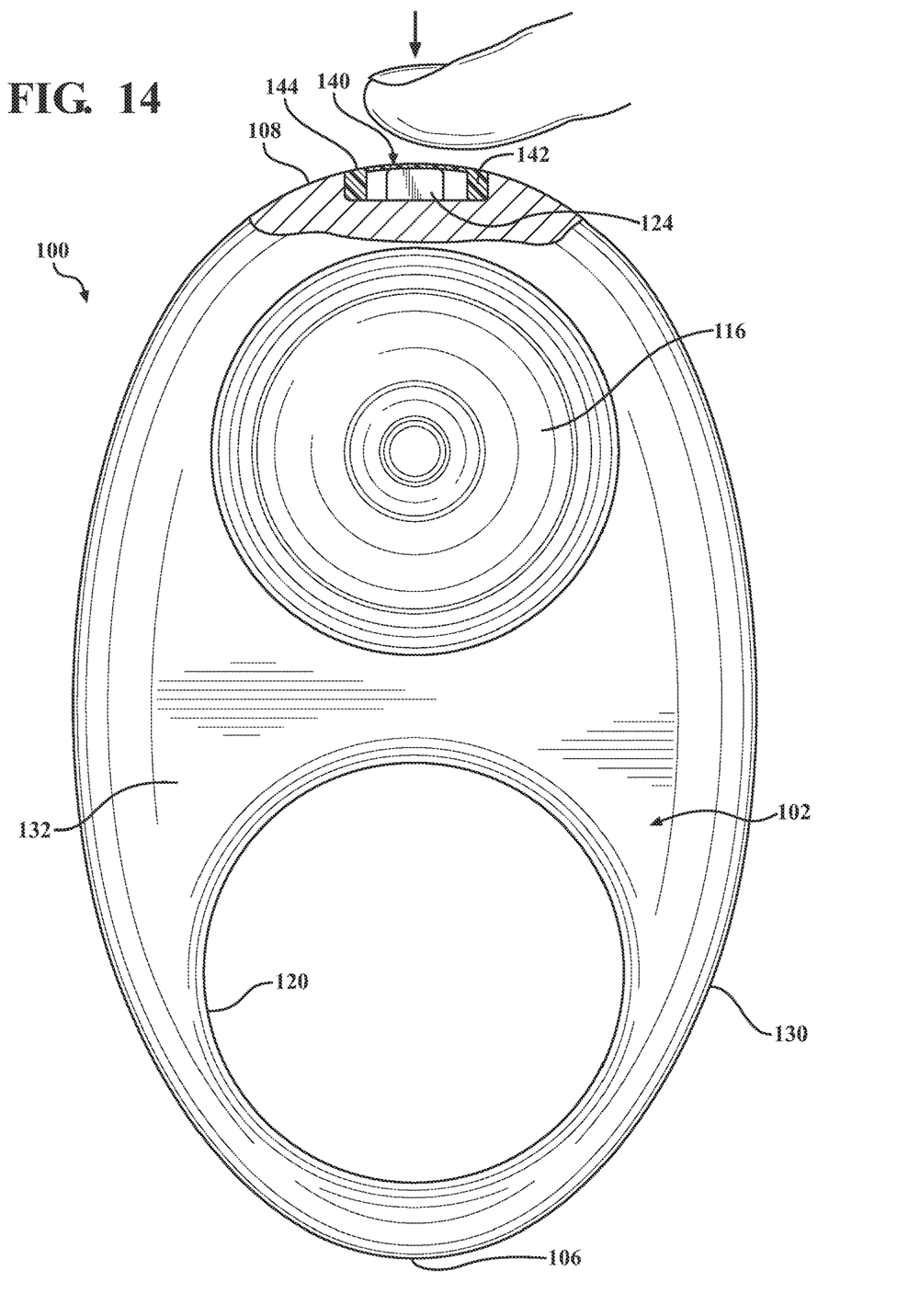
FIG. 14 is a front view of an alternative embodiment of the wearable ring.

Alluding to the above, the body 12 includes a side surface 30, a front surface 32 presenting a concave configuration and a rear surface 34 presenting a flat configuration. The body 12 is formed from a silicone material allowable to resiliently change forms of the body 12 to apply pressure to the penis P to hold erection and flex the body 12 to easily place in and remove out the camera 14. As shown in FIGS. 9 and 14, the body 12 may also include a second slot 36 defined in the rear surface 34 and a third slot 38 defined in the side surface 30 in case if other camera 14 may be used where an activation button may be located on the rear side or on the side wall of the camera 14.

Figure 1:
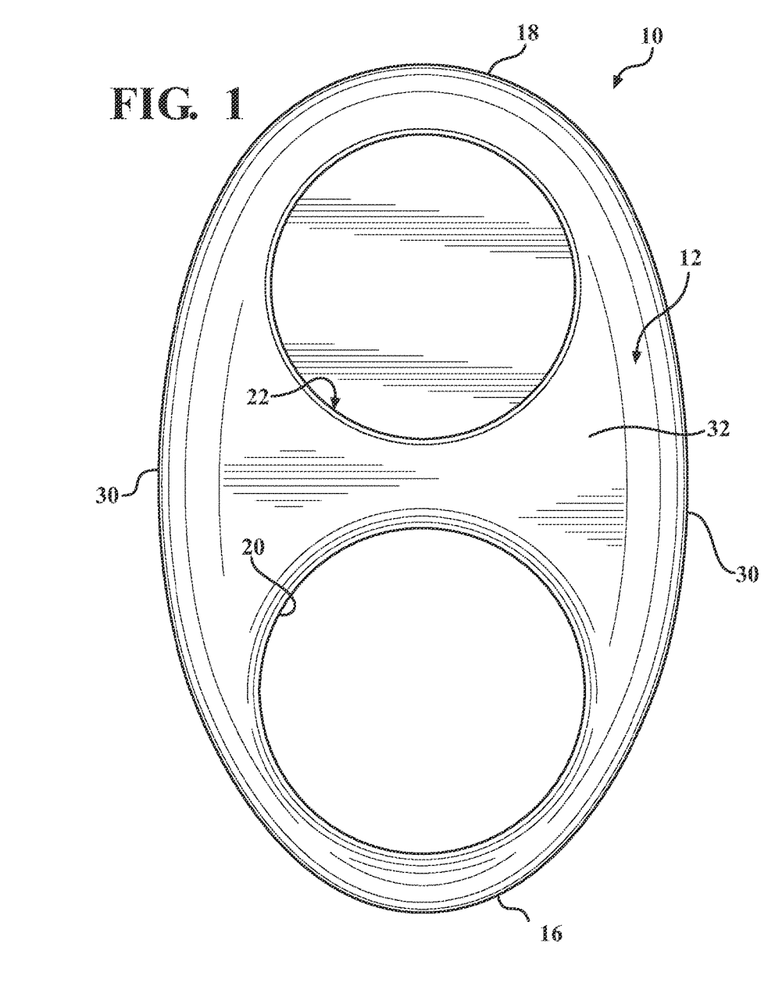
FIG. 1 is a front side view of a wearable ring for holding a camera.
Figure 2:
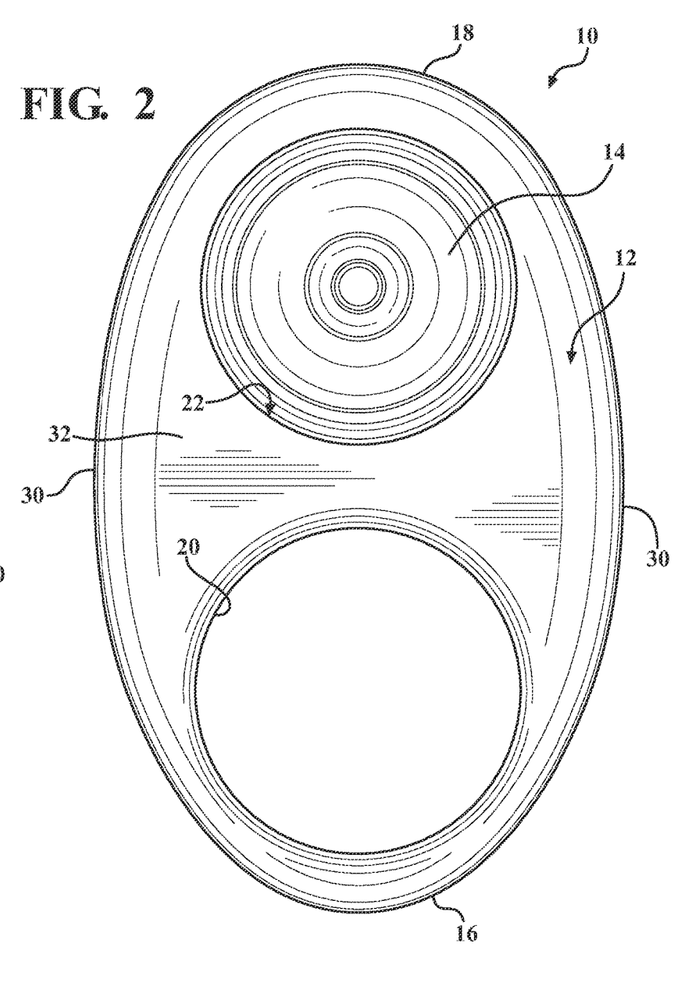
FIG. 2 is a front view of the wearable ring for holding the camera with the camera there inside.
Figure 3:
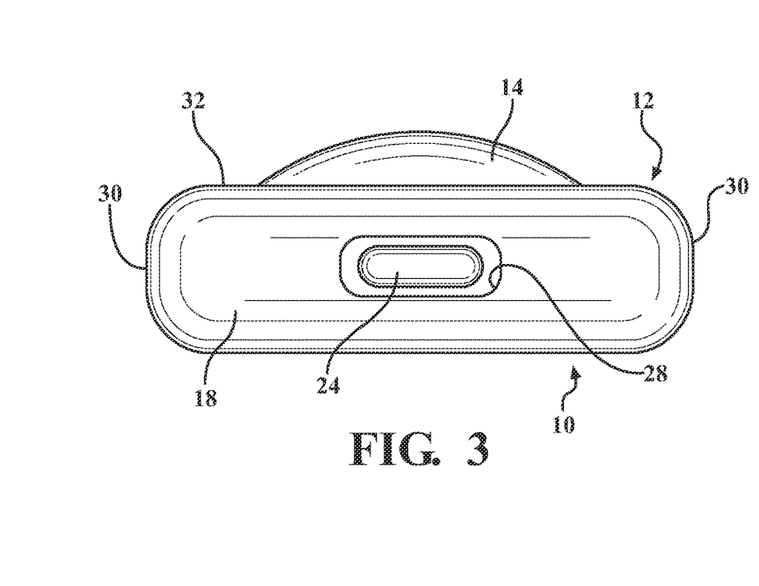
FIG. 3 is a top view of the wearable ring for holding the camera with the camera inside.
Figure 4:
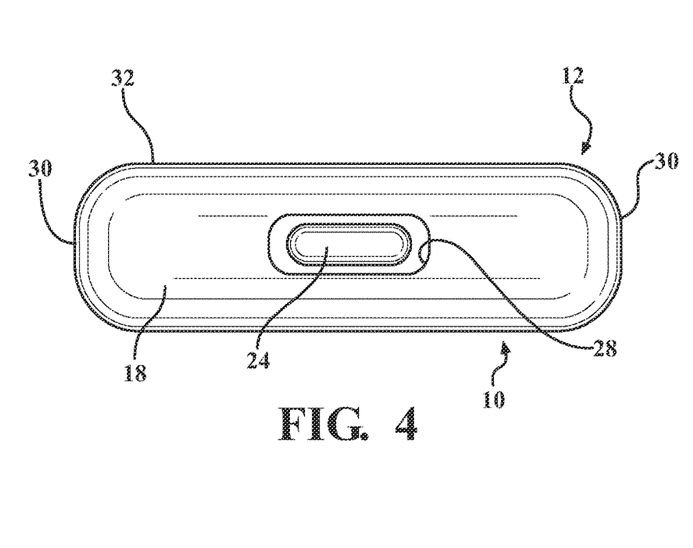
FIG. 4 is a top view of the wearable ring for holding the camera.
Figure 5:
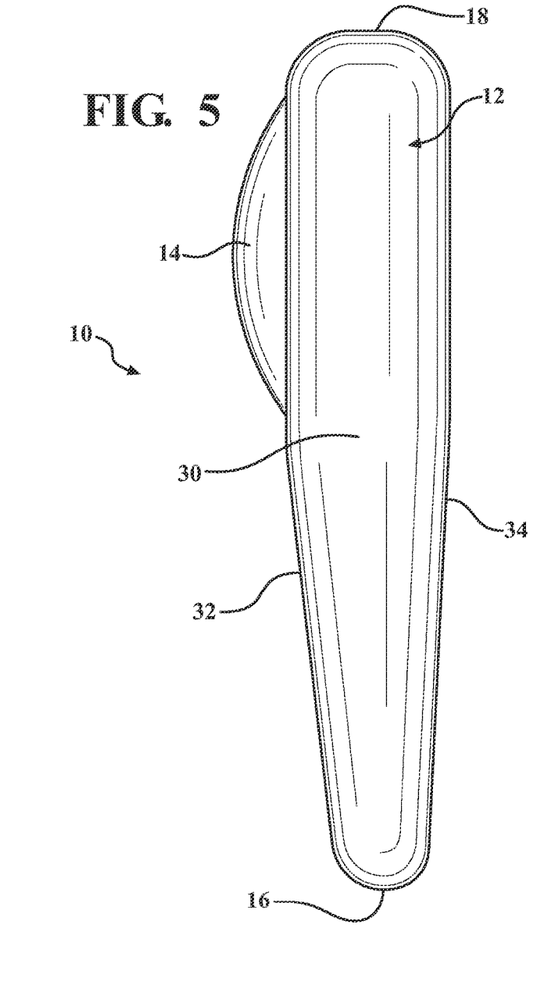
FIG. 5 is a right-side view of the wearable ring for holding the camera with the camera inside.
Figure 6:
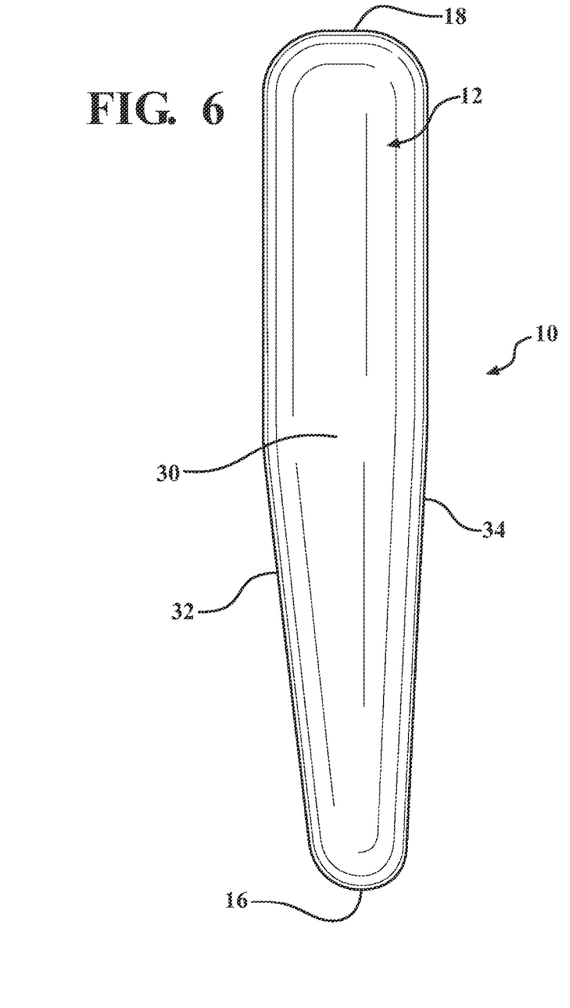
FIG. 6 is a right-side view of the wearable ring for holding the camera.
Figure 7:
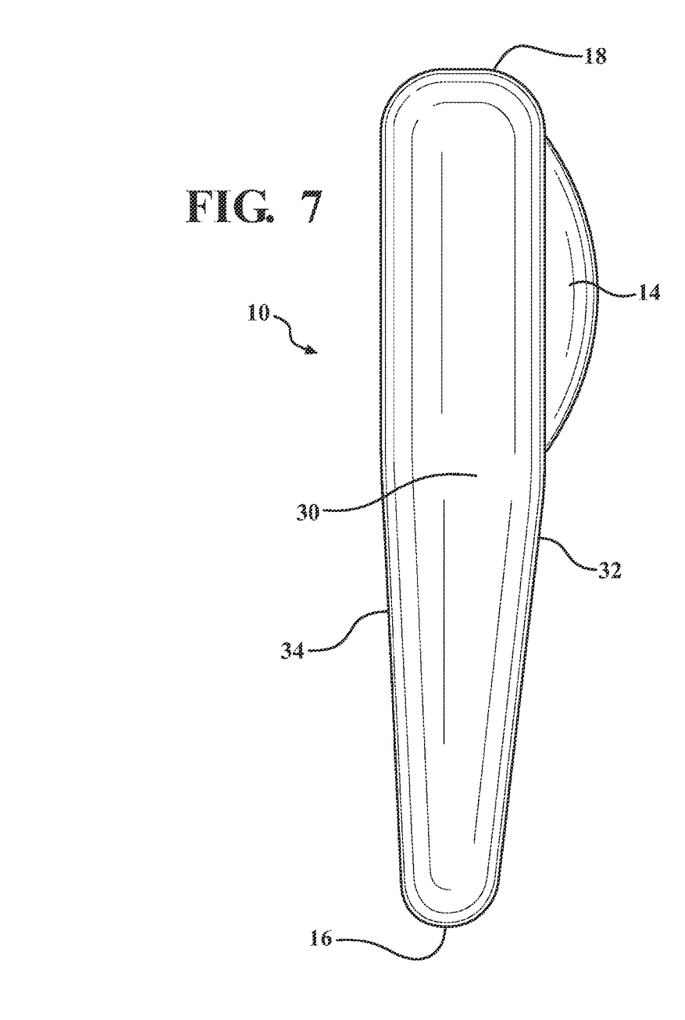
FIG. 7 is a left side view of the wearable ring for holding the camera with the camera inside.
Figure 8:
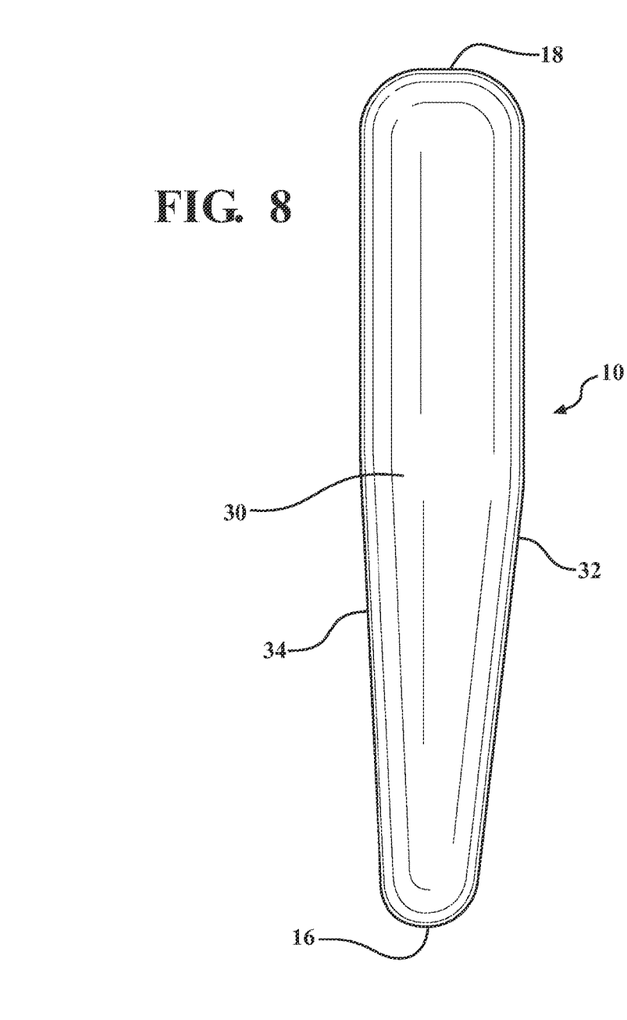
FIG. 8 is a left side view of the wearable ring for holding the camera.
Figure 13:
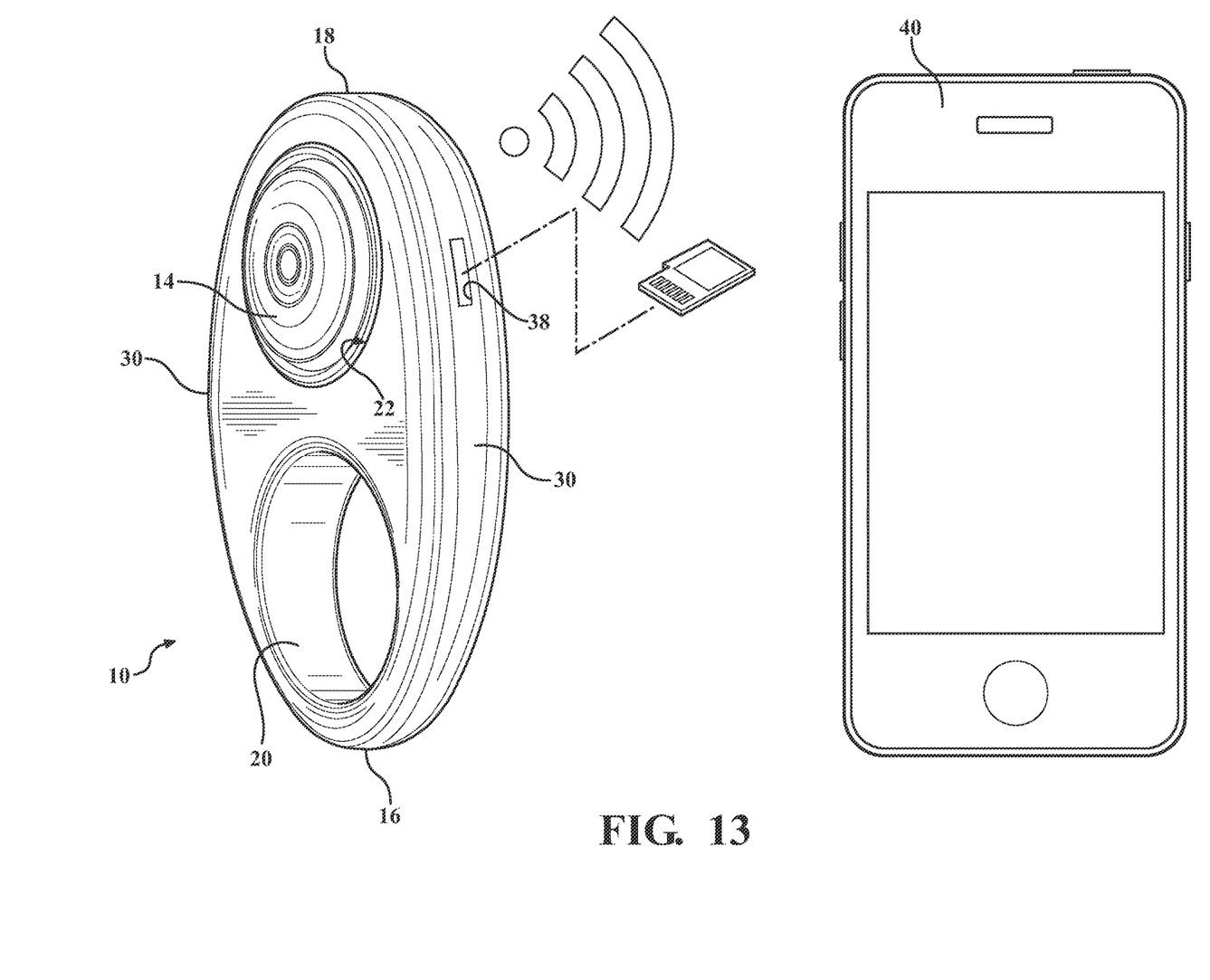
FIG. 13 illustrates a schematic view of the wearable ring for holding the camera operably communicated with a device such as a mobile phone.

The body 12 may be formed from other materials besides the silicone. The body 12 includes an oval configuration as shown in FIGS. 1 and 13, for example, wherein the camera 14 is a WiFi compatible camera, is wirelessly communicated with a personal computing device such as a personal computer and a mobile phone 40, so partners engaging in erotic relationship, can view the sexual act and enjoy the pleasure.

FIGS. 14 through 17, illustrates an alternative embodiment of a wearable device, such as a ring, generally shown at 100. The device 10 is designed as a silicone ring housing or a body, generally indicated at 102, which is wearable on a penis or dildo P, it is made in a way that it houses a WiFi compatible camera 104, which is controlled, viewed via a mobile application. The device 100 is used for sexual stimulation as well as recording intimate moments at a completely new angle and point of view.

FIGS. 14 through 17, the body 102 includes a bottom surface 106 and a top surface 108. An opening 120 is defined between the top surface 108 and the bottom surface 106. The opening 120 is used to receive therethrough and hold the at least one part of the human body, such as a finger or the penis P.

The body 102 includes a pocket section defined by a pair of pockets, generally indicated at 110 and 112 separated by a wall 114. The pocket section is defined in the body 102 between the opening 120 and the top surface 108 for holding a pair of cameras 116 and 118 each presenting an activation button 124 to turn on and turn off the cameras 116 and 118. The body 102 includes a side surface 130, a front surface 132 and a rear surface 134. The body 102 is formed from a silicone material allowable to resiliently change forms of the body 102 to apply pressure to the penis P to hold erection and flex the body 102 to easily place in and remove out the cameras 118 and 116.

Figure 15:
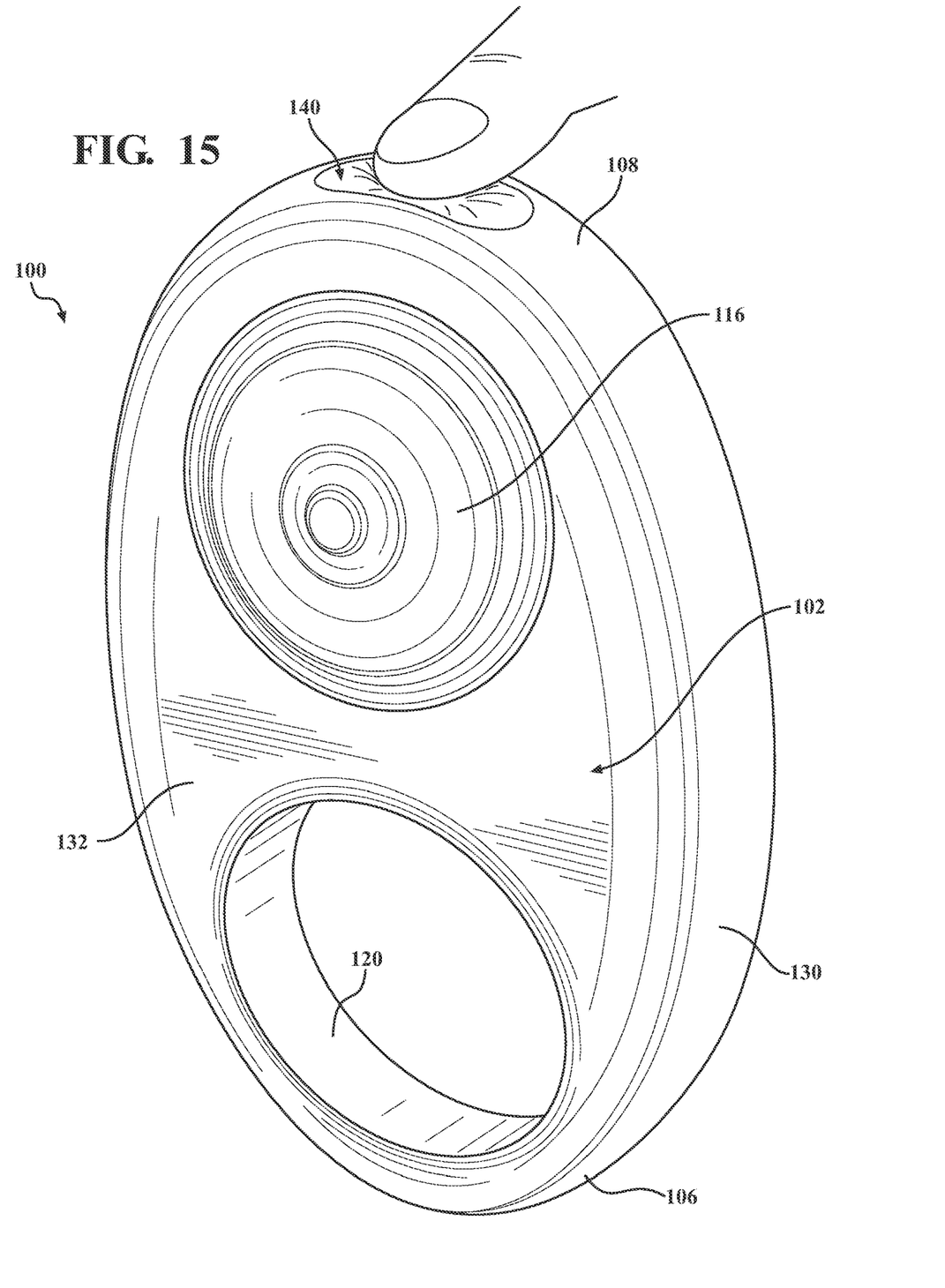
FIG. 15 is a perspective view of the alternative embodiment of the wearable ring shown in FIG. 14.
Figure 16:
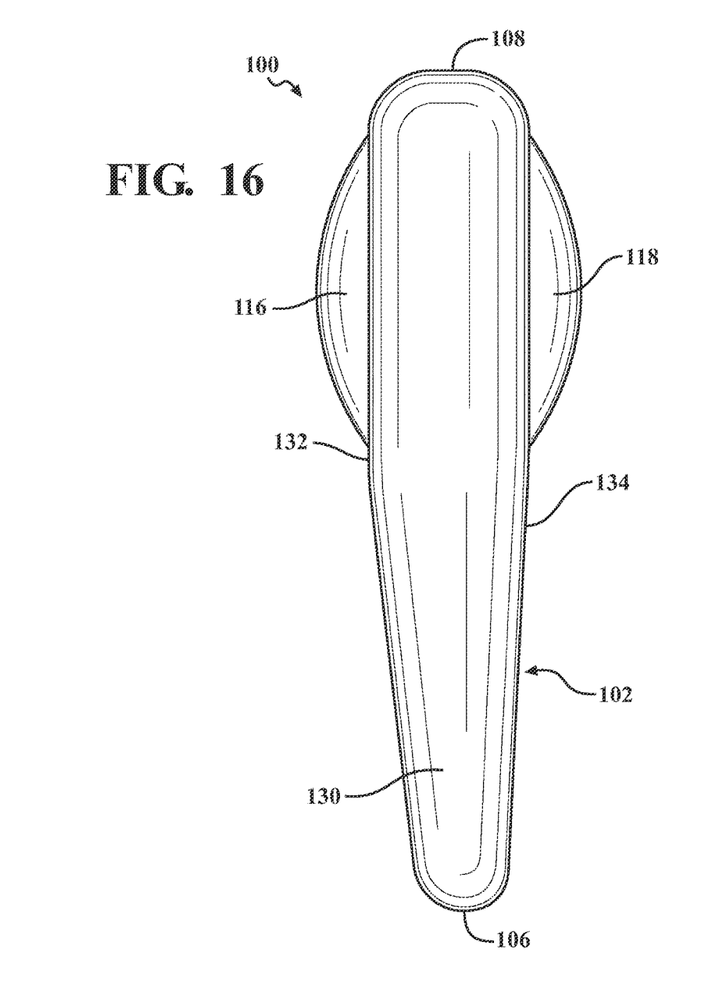
FIG. 16 is a side view of the alternative embodiment of the wearable ring shown in FIG. 14.
Figure 17:
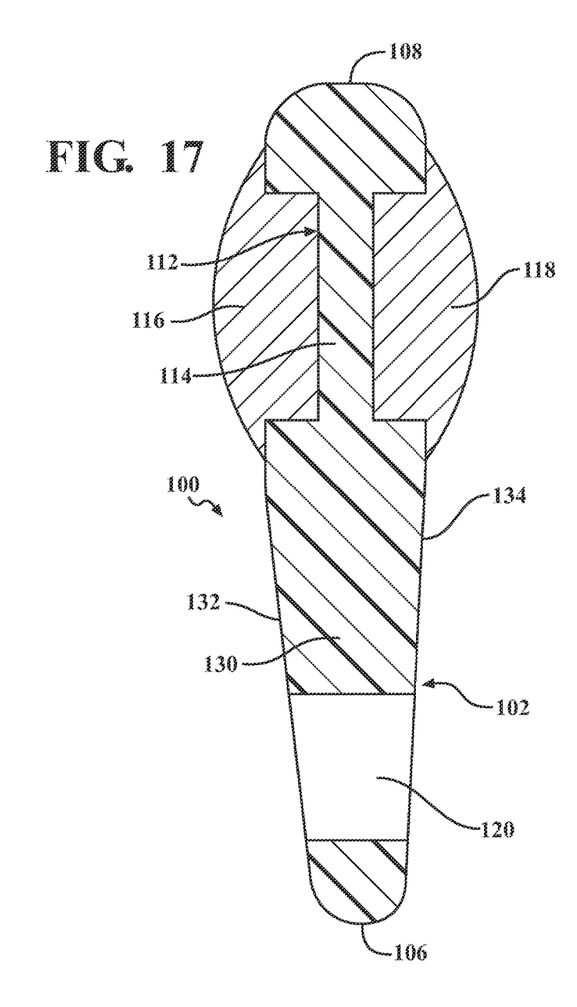
FIG. 17 is a side cross sectional view of the alternative embodiment of the wearable ring shown in FIG. 14 showing two pockets separated by a wall to house two cameras.

The body 102 includes a membrane, generally indicated at 140, defined in the top surface 108 of the body 102 wherein the at least one activation button 124 is located below the membrane 140 when the camera 116 or 118 is disposed in the respective pockets 110 and 112 to turn off or turn on the cameras 116 and 118. The top surface 108 includes a first section presenting a first thickness 142 and a second section presenting a second thickness 144. The second section is thinner that the first thickness. The membrane 140 is located around the second section 144, wherein, as at least one activation button 124 is activated. As best shown in FIGS. 14 and 15, the membrane 140 extends from an idle position as the first section. i.e., 142 and the second section, i.e. 144, are located along and coplanar with one another to an activating position, shown in FIG. 15, as the membrane 140 extends to and frictionally engages at least one activation button 124 to turn on the cameras 116 and 118 and returning back to the idle position.

Figure 18:
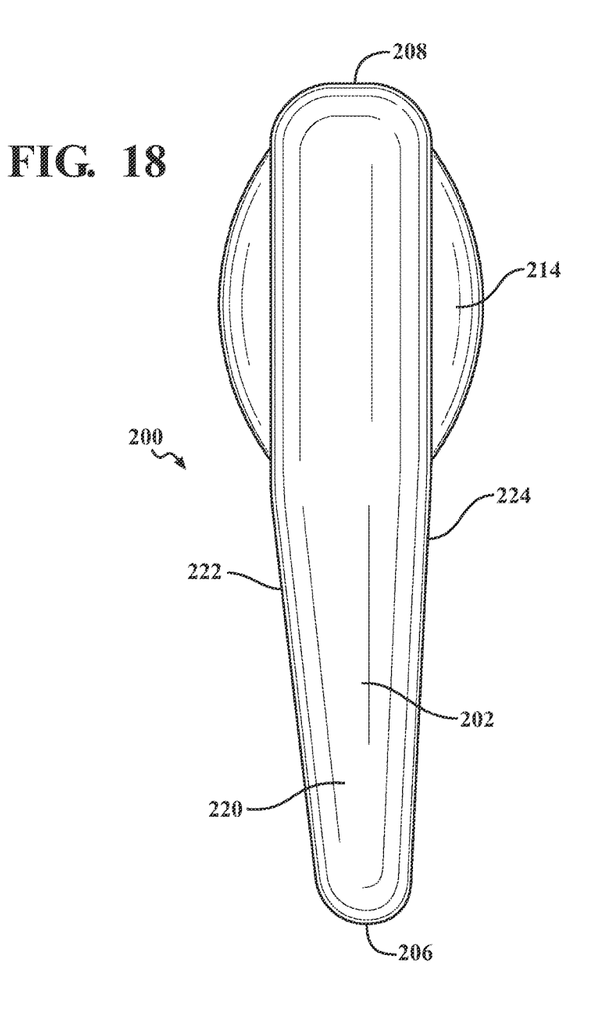
FIG. 18 is a side view of a second alternative embodiment of the wearable ring shown in FIG. 14.

FIG. 18 is a side view of a second alternative embodiment of the wearable ring shown in FIG. 14. The second alternative embodiment is generally shown at 200. The ring 200 the body 202 includes a bottom surface 206 and a top surface 208. An opening 210 is defined between the top surface 208 and the bottom surface 206. The opening 210 is used to receive therethrough and hold the at least one part of the human body, such as a finger or the penis P.

Figure 19:
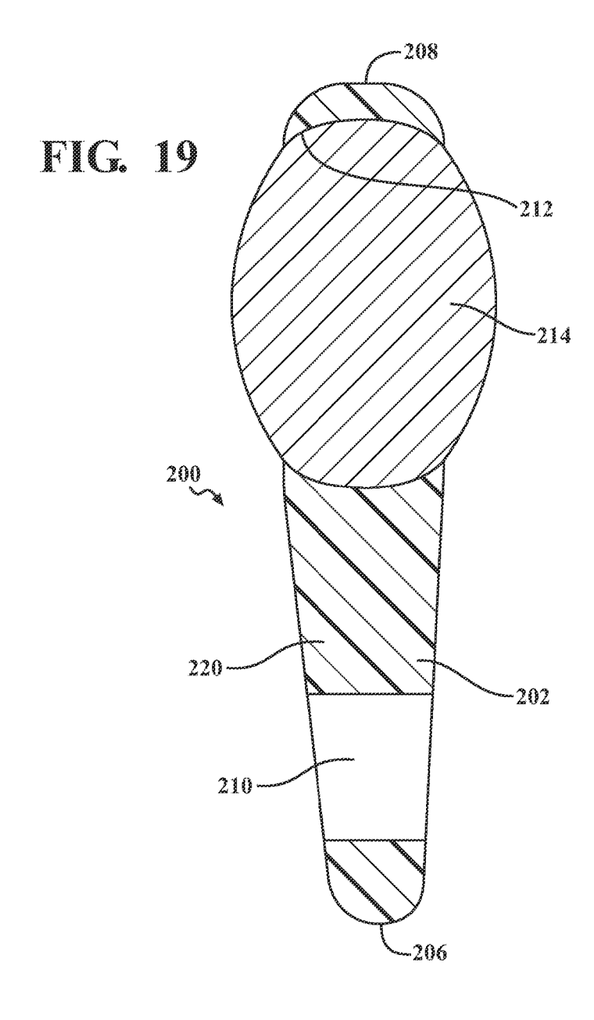
FIG. 19 is a side cross sectional view of the second alternative embodiment of the wearable ring shown in FIG. 18 showing a pocket extending through the body to house a 360 degrees camera.

The body 202 includes a pocket section 212. The pocket section is defined in the body 202 between the opening 210 and the top surface 208 for holding a 360-degree camera 214 presenting an activation button to turn on and turn off the camera 214. The body 202 includes a side surface 220, a front surface 222 and a rear surface 224. The body 202 is formed from a silicone material allowable to resiliently change forms of the body 202 to apply pressure to the penis P to hold erection and flex the body 202 to easily place in and remove out the camera 214.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A wearable device for at least one camera, said wearable device is used to be worn on at least one part of a human body, said wearable device comprising:
a body having a bottom surface and a top surface, said body presenting an opening defined between said top surface and said bottom surface, said opening is used to receive therethrough and hold the at least one part of the human body;
a first pocket defined in said body between said opening and said top surface for holding said at least one camera presenting at least one activation button to turn on and turn off said at least one camera; and
a membrane defined in said top surface of said body wherein said at least one activation button is located below said membrane as said at least one camera is disposed in said first pocket to turn off or turn on said at least one camera, said top surface includes a first section presenting a first thickness and a second section presenting a second thickness, said second section being thinner than said first thickness, said membrane located around said second thickness, wherein, as at least one activation button is activated, said membrane extends from an idle position as said first section and said second section are located along and coplanar with one another to an activating position as said membrane extends to and frictionally engages said at least one activation button to turn on said at least one camera and returning back to said idle position.

2. The wearable device of claim 1, wherein said body is formed from a silicone material allowable to resiliently change forms of said body.

3. The wearable device of claim 2, wherein said body presents an oval configuration.

4. The wearable device of claim 3, wherein said body includes a side surface extending between and interconnecting said top surface and said bottom surface.

5. The wearable device of claim 1, wherein said at least one camera is a WiFi compatible camera wirelessly communicated with a personal computing device such as a personal computer and a mobile phone.

6. The wearable device of claim 1, wherein said first pocket presents a circular configuration.

7. The wearable device of claim 6, wherein said body includes a front surface and a rear surface.

8. The wearable device of claim 7, wherein with said front surface is concave and said rear surface is flat.

9. The wearable device of claim 7, wherein said first pocket is formed in said front surface and a second pocket is formed in said rear surface to receive a second camera, said first pocket and said second pocket are spaced by a wall.

10. The wearable device of claim 1, wherein said first pocket extends through said body to receive a third camera being 360-degree camera.

11. The wearable device of claim 10, wherein said first pocket extends through said body to receive said 360-degree camera.

12. A wearable device for at least one camera, said wearable device is used to be worn on at least one part of a human body, said wearable device comprising:
a body having a bottom surface and a top surface, a side surface, a front surface presenting a concave configuration and rear surface presenting a flat configuration, said body formed from a silicone material allowable to resiliently change forms of said body;
said body presenting an opening defined between said top surface and said bottom surface, said opening is used to receive therethrough and hold the at least one part of the human body;
said at least one camera is a WiFi compatible camera wirelessly communicated with a personal computing device such as a personal computer and a mobile phone;
at least one pocket defined in said body between said opening and said top surface for holding said at least one camera presenting at least one activation button to turn on and turn off said at least one camera, said least one pocket presenting a circular configuration;
said body presenting a membrane defined in said top surface of said body wherein said at least one activation button located below said membrane as said camera is disposed in said least one pocket to turn off or turn on said at least one camera, said top surface includes a first section presenting a first thickness and a second section presenting a second thickness, said second section being thinner than said first thickness, said membrane located around said second thickness, wherein, as said at least one activation button is activated, said membrane extends from an idle position as said first section and said second section are located along and coplanar with one another to an activating position as said membrane extends to and frictionally engages said at least one activation button to turn on said at least one camera and returning back to said idle position; and
said first pocket is further defined by a pair of pockets opposite from one another with one of said pockets formed in said front surface and another pocket formed in said rear surface to receive a second camera, said pockets are spaced by a wall.

* * * * *